US008162896B2

(12) United States Patent
Tan

(10) Patent No.: US 8,162,896 B2
(45) Date of Patent: *Apr. 24, 2012

(54) FLASHBACK BLOOD COLLECTION NEEDLE

(75) Inventor: Chee Leong Tan, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/570,553

(22) Filed: Sep. 30, 2009

(65) Prior Publication Data

US 2010/0145226 A1    Jun. 10, 2010

Related U.S. Application Data

(63) Continuation of application No. 10/919,088, filed on Aug. 16, 2004, now Pat. No. 7,615,033.

(51) Int. Cl.
*A61M 5/178* (2006.01)

(52) U.S. Cl. .................... 604/168.01; 604/122; 604/126; 604/900; 600/573; 600/576; 600/577

(58) Field of Classification Search ............. 604/168.01, 604/122, 126, 900, 6.15, 6.16, 403, 404, 604/411; 600/573, 576–579, 581
See application file for complete search history.

(56) References Cited

U.S. PATENT DOCUMENTS

| | | |
|---|---|---|
| 1,779,451 A | 10/1930 | Sponsel |
| 2,004,050 A | 6/1935 | Kerk |
| 2,700,385 A | 1/1955 | Ortiz |
| 2,836,942 A | 6/1958 | Miskel |
| 2,854,976 A | 10/1958 | Heydrich |
| 2,953,243 A | 9/1960 | Roehr |
| 3,021,942 A | 2/1962 | Hamilton |
| 3,073,307 A | 1/1963 | Stevens |
| 3,074,542 A | 1/1963 | Myerson et al. |
| 3,255,873 A | 6/1966 | Speelman |
| 3,294,231 A | 12/1966 | Vanderbeck |
| 3,323,523 A | 6/1967 | Scislowicz et al. |
| 3,329,146 A | 7/1967 | Waldman, Jr. |
| 3,333,682 A | 8/1967 | Burke |
| 3,367,488 A | 2/1968 | Hamilton |
| 3,382,865 A | 5/1968 | Worrall, Jr. |
| 3,485,239 A | 12/1969 | Vanderbeck |
| 3,537,452 A | 11/1970 | Wilks |
| 3,585,984 A | 6/1971 | Buchanan |
| 3,610,240 A | 10/1971 | Harautuneian |
| 3,658,061 A | 4/1972 | Hall |

(Continued)

FOREIGN PATENT DOCUMENTS

EP    0060385 A1    9/1982

(Continued)

*Primary Examiner* — Jackie Ho
*Assistant Examiner* — Laura Schell
(74) *Attorney, Agent, or Firm* — David M. Fortunato

(57) ABSTRACT

A needle assembly includes a transparent or translucent housing with a fluid inlet end, a fluid outlet end, a flashback chamber and a venting mechanism therebetween. Substantially axially aligned inlet and outlet cannulas extend from the housing and communicate with the chamber. A sealable sleeve covers the external end of the outlet cannula. Relative volumes of the cannulas, the chamber and the sleeve are selected to provide rapid reliable flashback indicative of venous entry with an internal vent plug over the outlet of the flashback chamber to inhibit leakage of blood from the needle on withdrawal from the patient.

18 Claims, 7 Drawing Sheets

U.S. PATENT DOCUMENTS

| | | |
|---|---|---|
| 3,664,879 A | 5/1972 | Olsson |
| 3,817,240 A | 6/1974 | Ayres |
| 3,828,775 A | 8/1974 | Armel |
| 3,859,998 A | 1/1975 | Thomas et al. |
| 3,874,367 A | 4/1975 | Ayres |
| 3,886,930 A | 6/1975 | Ryan |
| 3,890,971 A | 6/1975 | Leeson et al. |
| 3,904,033 A | 9/1975 | Haerr |
| 3,934,722 A | 1/1976 | Goldberg |
| 3,968,876 A | 7/1976 | Brookfield |
| 4,106,497 A | 8/1978 | Percarpio |
| 4,108,175 A | 8/1978 | Orton |
| 4,113,090 A | 9/1978 | Carstens |
| 4,139,009 A | 2/1979 | Alvarez |
| 4,154,229 A | 5/1979 | Nugent |
| 4,166,450 A | 9/1979 | Abramson |
| 4,175,008 A | 11/1979 | White |
| 4,193,400 A | 3/1980 | Loveless et al. |
| 4,207,870 A | 6/1980 | Eldridge |
| 4,269,186 A | 5/1981 | Loveless et al. |
| 4,300,678 A | 11/1981 | Gyure et al. |
| 4,312,362 A | 1/1982 | Kaufman |
| 4,317,445 A | 3/1982 | Robinson |
| 4,340,068 A | 7/1982 | Kaufman |
| RE31,086 E | 11/1982 | Johnson, Jr. et al. |
| 4,375,849 A | 3/1983 | Hanifl |
| 4,398,544 A | 8/1983 | Nugent et al. |
| 4,409,990 A | 10/1983 | Mileikowsky |
| 4,412,548 A | 11/1983 | Hoch |
| 4,416,290 A | 11/1983 | Lutkowski |
| 4,416,291 A | 11/1983 | Kaufman |
| 4,418,703 A | 12/1983 | Hoch et al. |
| 4,430,082 A | 2/1984 | Schwabacher |
| 4,436,098 A | 3/1984 | Kaufman |
| 4,444,203 A | 4/1984 | Engelman |
| 4,592,744 A | 6/1986 | Jagger et al. |
| 4,634,428 A | 1/1987 | Cuu |
| 4,643,722 A | 2/1987 | Smith, Jr. |
| 4,659,330 A | 4/1987 | Nelson et al. |
| 4,664,249 A | 5/1987 | Gherardi |
| 4,664,654 A | 5/1987 | Strauss |
| 4,671,408 A | 6/1987 | Raines et al. |
| 4,679,571 A | 7/1987 | Frankel et al. |
| 4,681,567 A | 7/1987 | Masters et al. |
| 4,695,274 A | 9/1987 | Fox |
| 4,702,738 A | 10/1987 | Spencer |
| 4,723,943 A | 2/1988 | Spencer |
| 4,728,320 A | 3/1988 | Chen |
| 4,728,321 A | 3/1988 | Chen |
| 4,731,059 A | 3/1988 | Wanderer et al. |
| 4,735,311 A | 4/1988 | Lowe et al. |
| 4,735,618 A | 4/1988 | Hagen |
| 4,737,144 A | 4/1988 | Choksi |
| 4,738,663 A | 4/1988 | Bogan |
| 4,743,233 A | 5/1988 | Schneider |
| 4,746,008 A | 5/1988 | Heverly et al. |
| 4,747,836 A | 5/1988 | Luther |
| 4,747,837 A | 5/1988 | Hauck |
| 4,772,272 A | 9/1988 | McFarland |
| 4,778,453 A | 10/1988 | Lopez |
| 4,781,697 A | 11/1988 | Slaughter |
| 4,782,841 A | 11/1988 | Lopez |
| 4,788,986 A | 12/1988 | Harris |
| 4,790,828 A | 12/1988 | Dombrowski et al. |
| 4,793,484 A | 12/1988 | Schoettle |
| 4,795,432 A | 1/1989 | Karczmer |
| 4,795,443 A | 1/1989 | Permenter et al. |
| 4,801,295 A | 1/1989 | Spencer |
| 4,804,372 A | 2/1989 | Laico et al. |
| 4,813,426 A | 3/1989 | Haber et al. |
| 4,816,022 A | 3/1989 | Poncy |
| 4,816,024 A | 3/1989 | Sitar et al. |
| 4,819,659 A | 4/1989 | Sitar |
| 4,820,277 A | 4/1989 | Norelli |
| 4,826,490 A | 5/1989 | Byrne et al. |
| 4,826,491 A | 5/1989 | Schramm |
| 4,838,871 A | 6/1989 | Luther |
| 4,842,587 A | 6/1989 | Poncy |
| 4,844,089 A | 7/1989 | Roberti |
| 4,846,796 A | 7/1989 | Carrell et al. |
| 4,850,968 A | 7/1989 | Romano |
| 4,850,976 A | 7/1989 | Heinrich et al. |
| 4,850,977 A | 7/1989 | Bayless |
| 4,850,978 A | 7/1989 | Dudar et al. |
| 4,850,994 A | 7/1989 | Zerbst et al. |
| 4,850,996 A | 7/1989 | Cree |
| 4,858,607 A | 8/1989 | Jordan et al. |
| 4,863,434 A | 9/1989 | Bayless |
| 4,863,435 A | 9/1989 | Sturman et al. |
| 4,863,436 A | 9/1989 | Glick |
| 4,865,592 A | 9/1989 | Rycroft |
| 4,867,746 A | 9/1989 | Dufresne |
| 4,872,552 A | 10/1989 | Unger |
| 4,874,383 A | 10/1989 | McNaughton |
| 4,874,384 A | 10/1989 | Nunez |
| 4,883,469 A | 11/1989 | Glazier |
| 4,886,072 A | 12/1989 | Percarpio et al. |
| 4,886,503 A | 12/1989 | Miller |
| 4,888,001 A | 12/1989 | Schoenberg |
| 4,892,107 A | 1/1990 | Haber |
| 4,892,521 A | 1/1990 | Laico et al. |
| 4,894,052 A | 1/1990 | Crawford |
| 4,900,309 A | 2/1990 | Netherton et al. |
| 4,909,791 A | 3/1990 | Norelli |
| 4,909,792 A | 3/1990 | Norelli |
| 4,921,096 A | 5/1990 | McFarlane |
| 4,927,018 A | 5/1990 | Yang et al. |
| 4,944,397 A | 7/1990 | Miller |
| 4,966,591 A | 10/1990 | Yuen |
| 4,971,068 A | 11/1990 | Sahi |
| 4,976,699 A | 12/1990 | Gold |
| 4,982,842 A | 1/1991 | Hollister |
| 5,011,475 A | 4/1991 | Olson |
| 5,011,479 A | 4/1991 | Le et al. |
| 5,030,207 A | 7/1991 | Mersch et al. |
| 5,032,116 A | 7/1991 | Peterson et al. |
| 5,033,476 A | 7/1991 | Kasai |
| 5,055,102 A | 10/1991 | Sitnik |
| 5,069,225 A | 12/1991 | Okamura |
| 5,078,693 A | 1/1992 | Shine |
| 5,078,698 A | 1/1992 | Stiehl et al. |
| 5,092,845 A | 3/1992 | Chang |
| 5,112,327 A | 5/1992 | Iinuma et al. |
| 5,116,325 A | 5/1992 | Paterson |
| 5,120,319 A | 6/1992 | Van Heugten et al. |
| 5,122,121 A | 6/1992 | Sos et al. |
| 5,135,509 A | 8/1992 | Olliffe |
| 5,137,518 A | 8/1992 | Mersch |
| 5,139,489 A | 8/1992 | Hollister |
| 5,151,089 A | 9/1992 | Kirk, III et al. |
| 5,154,285 A | 10/1992 | Hollister |
| 5,181,523 A | 1/1993 | Wendelborn |
| 5,188,611 A | 2/1993 | Orgain |
| 5,197,954 A | 3/1993 | Cameron |
| 5,201,794 A | 4/1993 | Kasai et al. |
| 5,207,653 A | 5/1993 | Janjua et al. |
| 5,217,025 A | 6/1993 | Okamura |
| 5,222,502 A | 6/1993 | Kurose |
| 5,232,454 A | 8/1993 | Hollister |
| 5,232,455 A | 8/1993 | Hollister |
| 5,242,411 A | 9/1993 | Yamamoto et al. |
| 5,242,417 A | 9/1993 | Paudler |
| 5,277,311 A | 1/1994 | Hollister |
| 5,290,246 A | 3/1994 | Yamamoto et al. |
| 5,295,969 A | 3/1994 | Fischell et al. |
| 5,303,713 A | 4/1994 | Kurose |
| 5,306,259 A | 4/1994 | Fischell et al. |
| 5,312,369 A | 5/1994 | Arcusin et al. |
| 5,401,251 A | 3/1995 | Hui |
| 5,405,332 A | 4/1995 | Opalek |
| 5,423,765 A | 6/1995 | Hollister |
| 5,450,856 A | 9/1995 | Norris |
| 5,462,534 A | 10/1995 | Debreczeni |
| 5,485,854 A | 1/1996 | Hollister |
| 5,486,163 A | 1/1996 | Haynes |
| 5,490,841 A | 2/1996 | Landis |
| 5,496,281 A | 3/1996 | Krebs |

| | | |
|---|---|---|
| 5,509,907 A | 4/1996 | Bevilacqua |
| 5,520,193 A | 5/1996 | Suzuki et al. |
| 5,533,984 A | 7/1996 | Parmigiani |
| 5,542,932 A | 8/1996 | Daugherty |
| 5,584,816 A | 12/1996 | Gyure et al. |
| 5,599,313 A | 2/1997 | Gyure et al. |
| 5,599,318 A | 2/1997 | Sweeney et al. |
| 5,603,699 A | 2/1997 | Shine |
| 5,632,732 A | 5/1997 | Szabo et al. |
| 5,643,219 A | 7/1997 | Burns |
| 5,662,617 A | 9/1997 | Odell et al. |
| 5,665,075 A | 9/1997 | Gyure et al. |
| 5,669,889 A | 9/1997 | Gyure et al. |
| 5,693,022 A | 12/1997 | Haynes |
| 5,697,914 A | 12/1997 | Brimhall |
| 5,702,369 A | 12/1997 | Mercereau |
| 5,733,265 A | 3/1998 | Bachman et al. |
| 5,755,701 A | 5/1998 | Sarstedt |
| 5,807,351 A | 9/1998 | Kashmer |
| 5,830,190 A | 11/1998 | Howell |
| 5,836,920 A | 11/1998 | Robertson |
| 5,885,249 A | 3/1999 | Irisawa |
| 5,893,844 A | 4/1999 | Misawa |
| 5,913,846 A | 6/1999 | Szabo |
| 5,984,895 A | 11/1999 | Padilla et al. |
| 5,993,426 A | 11/1999 | Hollister |
| 6,059,737 A | 5/2000 | Crawford |
| 6,077,244 A | 6/2000 | Botich et al. |
| 6,077,253 A | 6/2000 | Cosme |
| 6,080,137 A | 6/2000 | Pike |
| 6,096,006 A | 8/2000 | Sarstedt et al. |
| 6,110,160 A | 8/2000 | Farber |
| 6,120,482 A | 9/2000 | Szabo |
| 6,156,010 A | 12/2000 | Kuracina et al. |
| 6,190,370 B1 | 2/2001 | Tsui |
| 6,261,263 B1 | 7/2001 | Huet et al. |
| 6,511,439 B1 | 1/2003 | Tabata et al. |
| 6,533,760 B2 | 3/2003 | Leong |
| 6,964,658 B2 | 11/2005 | Ashby et al. |
| 7,160,267 B2 | 1/2007 | Brown |
| 7,226,432 B2 * | 6/2007 | Brown .......................... 604/122 |

FOREIGN PATENT DOCUMENTS

| | | |
|---|---|---|
| EP | 0139872 A1 | 5/1985 |
| EP | 0619096 A1 | 10/1994 |
| JP | 58183172 | 10/1983 |
| JP | 58188460 A | 11/1983 |
| JP | 58212454 A | 12/1983 |
| JP | 04132541 | 5/1992 |
| JP | 04364831 | 12/1992 |
| JP | 06007330 | 1/1994 |
| JP | 07039541 | 2/1995 |
| JP | 0713304 | 3/1995 |
| JP | 0739804 | 7/1995 |
| JP | 08150134 | 6/1996 |
| JP | 08257018 | 10/1996 |
| JP | 08275933 | 10/1996 |
| JP | 11028200 | 2/1999 |
| JP | 11169359 | 6/1999 |
| JP | 2000023948 A | 1/2000 |
| JP | 2000139879 | 5/2000 |
| JP | 2000166903 | 6/2000 |
| JP | 2001000424 | 1/2001 |
| JP | 2001299728 | 10/2001 |
| JP | 2001299729 | 10/2001 |
| WO | 9903417 A1 | 1/1999 |

* cited by examiner

FLASHBACK BLOOD COLLECTION NEEDLE

The present application is a Continuation application based upon U.S. application Ser. No. 10/919,088, filed Aug. 16, 2004, entitled "Flashback Blood Collection Needle", now U.S. Pat. No. 7,615,033.

BACKGROUND OF THE INVENTION

1. Field of the Invention

The present invention relates to a device for collecting blood samples by performing venipuncture on a patient. More particularly, the present invention relates to a needle assembly for multiple sample blood collection that allows a phlebotomist to determine whether vein entry has occurred when collecting a blood sample from a patient into an evacuated blood collection tube.

2. Description of Related Art

Venipuncture is the primary method used for acquiring blood samples for laboratory testing. In performing venipuncture procedures, a phlebotomist must follow several steps simultaneously. Such steps include assessing the patient's overall physical and psychological condition so as to properly select a venipuncture site and technique. The phlebotomist must also select the proper corresponding equipment, perform the technique so as to control bleeding, and properly collect and identify fluid specimens for testing. The phlebotomist must ascertain all of these coinciding factors, as such factors may adversely affect the distension of the vein and the length of the venipuncture procedure.

Various venipuncture devices have been developed to address the above-described problems. These devices include products intended to assist the phlebotomist in confirming that vein entry has been made see e.g. U.S. Pat. Nos. 5,222, 502 and 5,303,713. Such a device contains a needle assembly with a housing that defines a chamber therein. A single cannula pointed at both ends, is affixed to the housing. The intravenous (IV) end of the cannula is adapted for penetration of a patient's vein. The non-patient end of the cannula has a sealable sleeve and is adapted for penetration of a penetrable stop positioned within an evacuated container.

Upon vein entry with the intravenous end of the cannula, blood will flow through the cannula, into the sealable sleeve and into the housing chamber, which is clear or translucent for visualization ("flashback"). Once air is vented from the flashback chamber, the blood therein is pressurized each time the sealable sleeve is pushed toward the housing chamber upon activation of an evacuated container.

Due to the length of time between vein entry and flashback, the phlebotomist may erroneously believe that satisfactory vein entry has not been achieved since there is no immediate indication of vein entry in the see-through chamber. The phlebotomist may therefore unnecessarily repeat the venipuncture procedure, requiring replacement of the evacuated container and/or the needle assembly itself. Such a repetitive process prolongs the physical and emotional discomfort endured by the patient. In such cases, a phlebotomist may use a blood collection set to provide some entry indication, and will then incur the cost of the blood collection set, as well as the cost of a discard tube.

It would therefore be desirable to provide an improved blood collection device that permits blood flow through a relatively short needle directly into a flashback chamber, thereby providing immediate indication of successful vein entry.

SUMMARY OF THE INVENTION

The invention provides a needle assembly for the extraction of at least one fluid sample into an evacuated container for laboratory testing. The needle assembly provides a clear or translucent housing with sufficient dead space for blood to flow into a flashback chamber for visualization by the user to confirm successful vein entry, with an internal vent mechanism over the outlet of the flashback chamber to inhibit leakage of blood from the IV needle on withdrawal from the patient. As used herein vent mechanism indicates one or more features or elements that provide venting of air, but which, typically, prevent fluid from passing through. The actual element that vents the air in the venting mechanism may be for example a vent plug or a one-way valve. At the same time there will be very little residual blood in the housing after use as the vent mechanism retains the blood within the relatively small flashback chamber.

According to the invention a needle assembly includes a housing which in turn is comprised of a housing interior, a flashback chamber in communication with the housing interior; and either (i) a first cannula mounted in the housing in communication with the flashback chamber and a second cannula mounted in the housing in communication with the flashback chamber, or (ii) a single cannula mounted in the housing with an opening in communication with the flashback chamber. These elements are configured such that the sole communication path between the housing interior and the external environment is via the flashback chamber. A vent mechanism is located in the communication path between the flashback chamber and the housing interior; so that upon contact with blood, this venting mechanism seals against the flow of air from the housing interior into the flashback chamber.

In use, the intravenous (IV) cannula (or IV portion of a single cannula). punctures the patient's skin to make a vein entry. Upon satisfactory vein entry, air that is at atmospheric pressure within the lumen of the IV cannula, flashback chamber, housing interior and the lumen of the non-patient cannula (or non-patient portion of a single cannula) experiences compression due to the influence of venous pressure and therefore flows through the IV cannula into the flashback chamber and through the vent plug into housing interior. Because the venous pressure exceeds the atmospheric pressure within flashback chamber, blood flows into the chamber. Blood flow into the housing interior is prevented by the vent mechanism, which while allowing air to flow through it, seals on contact with blood thereby trapping the compressed air at venous pressure in the housing interior. This inhibits leakage of the blood or fluid sample from the N cannula on removal from the patient, which might otherwise occur due to decompression of the air from the housing interior through the N cannula.

The volumes defined by the lumens through the cannulas, the chamber, the housing interior and the sleeve are selected to achieve a very rapid indication of vein entry. The first and second cannulas are typically in axial alignment with one another to provide an axial fluid flow path therebetween along a length of the housing. The second cannula typically includes a sealable sleeve.

DETAILED DESCRIPTION

The invention provides a needle assembly for blood collection that, provides a visual indication of vein entry ("flashback") upon collection of a blood or other fluid sample from a patient into one or more evacuated blood collection tubes and inhibits leakage of the blood or fluid sample from the IV cannula on removal from the patient.

Figure 1:
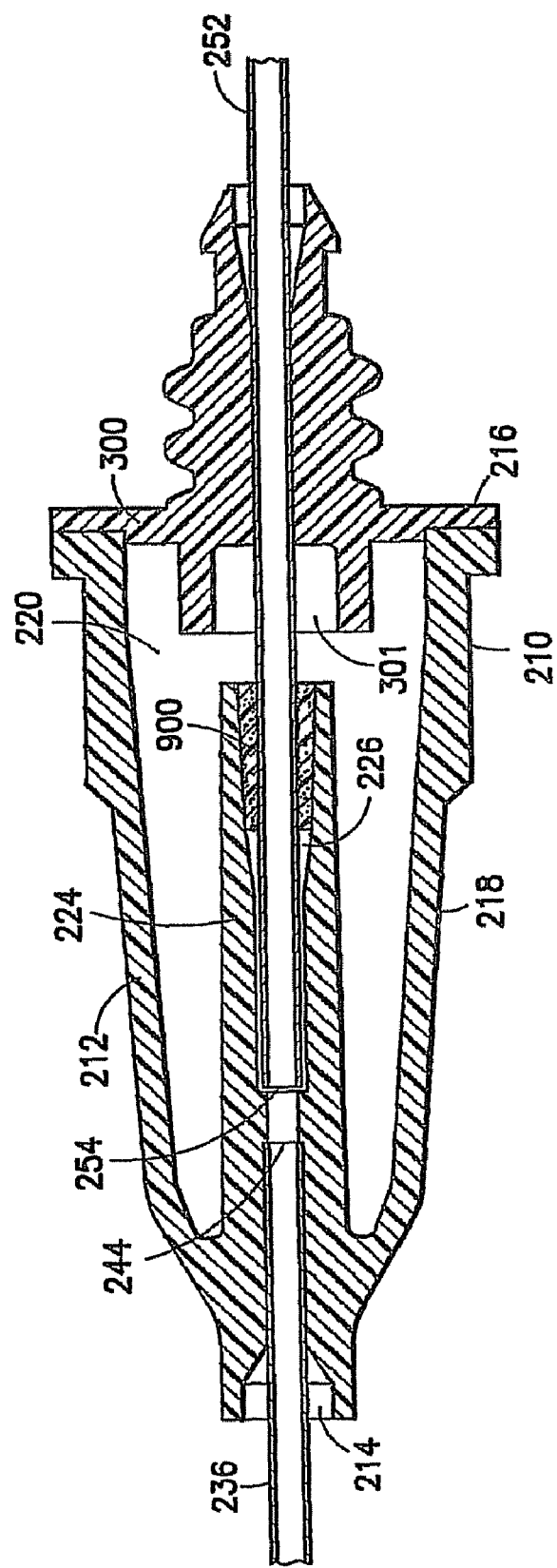
FIG. 1 is a cross-sectional view of a typical embodiment of the needle assembly of the present invention.

Various embodiments of the present invention are shown in FIGS. 1-7, With reference to FIG. 1, this embodiment is directed to a needle assembly 210 with a housing 212 having a fluid inlet end 214, a fluid outlet end 216 and a frustum-shaped exterior wall 218 extending between the ends. Exterior wall 218 defines the housing interior 220. Housing 212 further includes a cylindrical interior wall 224 that extends in the housing interior 220 from fluid inlet end 214 substantially concentrically with cylindrical exterior wall 218 to a vent plug 900. Cylindrical interior wall 224 and vent plug 900 define a flashback chamber 226.

Needle assembly 210 also includes a fluid inlet cannula 236 having an exterior end that defines a sharpened bevel and an interior end 244 that is mounted fixedly in fluid inlet end 214 of housing 212. Fluid inlet cannula 236 is characterized further by a substantially cylindrical lumen extending between the ends and communicating with the interior of housing 212.

Needle assembly 210 further includes a fluid outlet cannula 252. Outlet cannula 252 concludes a blunt interior end 254, an exterior end defining a sharpened bevel and a substantially cylindrical lumen extending between the ends. Portions of outlet cannula 252 between the ends are securely affixed in outlet end 216 of housing 212. Outlet cannula 252 is mounted so that interior end 254 passes substantially coaxially into interior wall 224 and so that interior end 254 of outlet cannula 252 substantially aligns axially with interior end 244 of inlet cannula 236. Additionally, interior end 254 of outlet cannula 252 is spaced only a small distance from interior end 244 of inlet cannula 236. An axial gap between interior end 254 of outlet cannula 252 and interior end 244 of inlet cannula 236 that is less than 0.5 mm may result in a flashback that is inconsistent.

Cylindrical interior wall 224 is dimensioned relative to outlet cannula 252 to achieve both desirable flow of blood through assembly 210 and to achieve effective flashback indication. In particular, cylindrical interior wall 224 preferably is dimensioned to provide a radial gap around outlet cannula 252 of about 0.2 mm, as indicated by dimension "c" in FIG. 1. This gap achieves a substantially laminar blood flow within flashback chamber 226 and prevents blood hemolysis. Additionally, the small radial gap between cylindrical inner wall 224 and outlet cannula 252 enables a drop of blood to be spread thinly across the radial gap in flashback chamber 226 to provide a magnified flashback indication with a very small volume of blood. Thus, an easily visualized flashback indication is achieved quickly at the first appearance of blood from interior end 244 of inlet cannula 236.

Needle assembly 210 further includes a sealable sleeve 261 mounted to fluid outlet end 216 of housing 212 and covering exterior end 258 of outlet cannula 252 when sealable sleeve 261 is in an unbiased condition. However, sealable sleeve 261 can be collapsed in response to pressure exerted by the stopper of an evacuated tube for urging exterior end 260 of outlet cannula 252 through both sealable sleeve 261 and stopper of an evacuated tube, as known in the art.

The above embodiment is described in terms of a vent plug. However, any vent mechanism is suitable. The vent mechanism may be, for example, a porous vent plug formed from a matrix or carrier material, typically hydrophobic, that is coated with, impregnated with, or otherwise, contains a hydrophilic material that swells on contact with aqueous or water containing substances. The hydrophobic carrier material can be but is not limited too, high-density polyethylene, polytetrafluoroethylene, ultra-high molecular weight polyethylene, Nylon 6, polypropylene, polyvinylidine fluoride and polyethersulfone. The swellable nature of the hydrophilic material thereby provides the sealing function in the vent upon contact with blood. It is also possible to use a porous vent plug that becomes sealed upon contact with blood using biological phenomena, e.g., by clotting and/or cell agglutination that blocks the vent; a superabsorbant material to seal the vent by swelling on contact with an aqueous fluid; or a one-way valve, (e.g., a thin flap such as plastic film covering a vent, a deformable seal such as a rubber or plastic duckbill valve, or a deformable wrap over a vent). Is should be noted that any combination of these various mechanisms is also possible.

Figure 2:
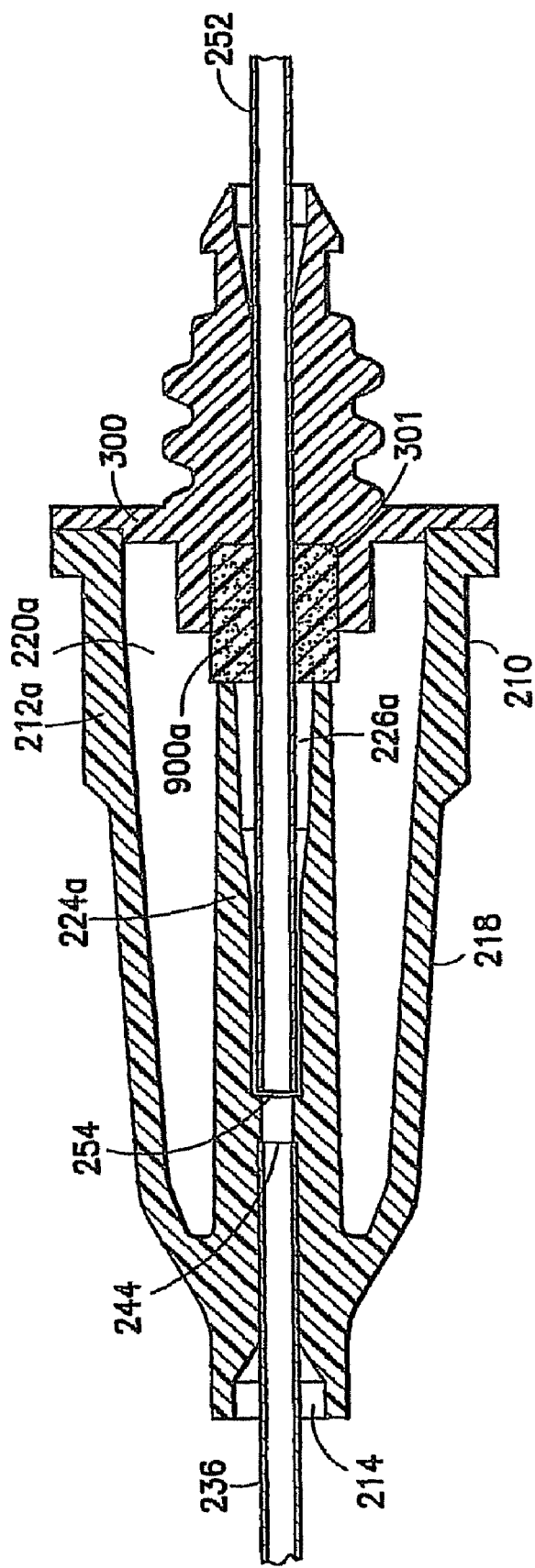
FIG. 2 is a cross-sectional view of a second embodiment.
Figure 3:
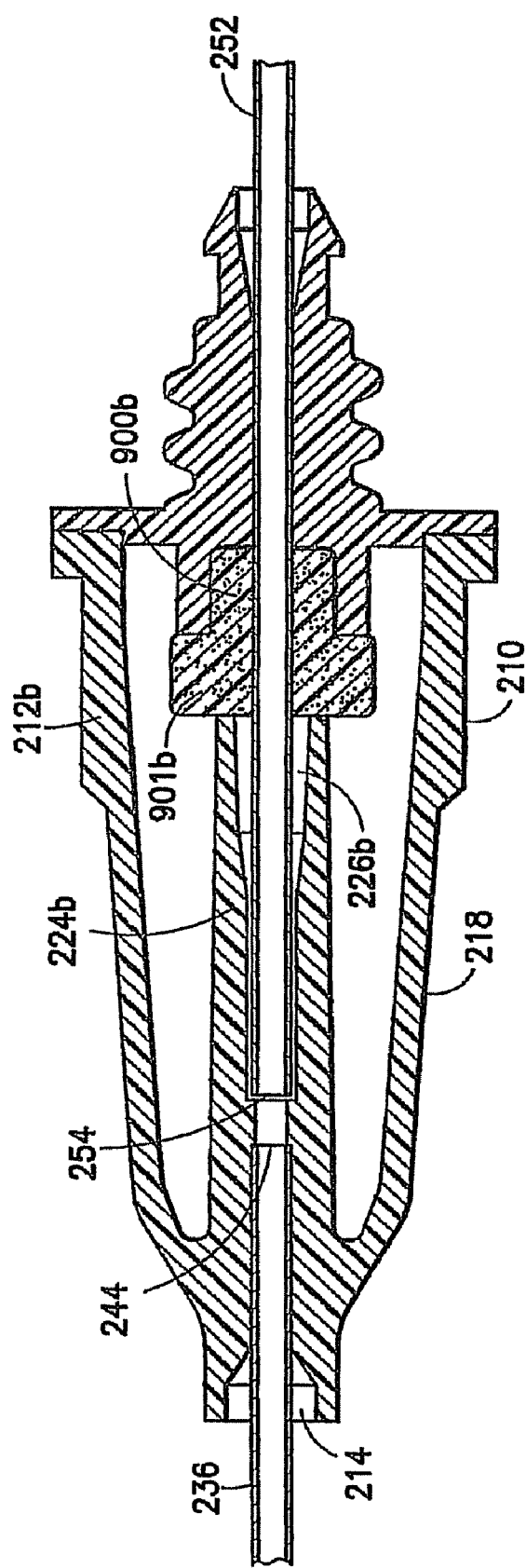
FIG. 3 is a cross-sectional view of a third embodiment.
Figure 4:
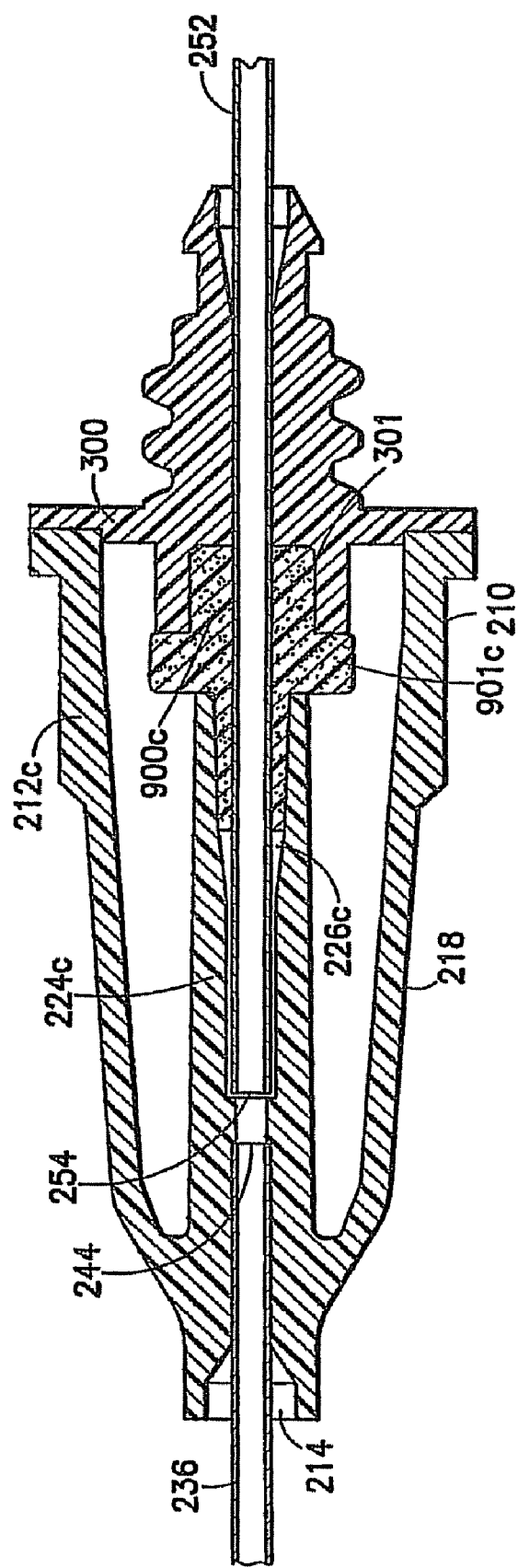
FIG. 4 is a cross-sectional view of a fourth embodiment.

FIGS. 2-4 show embodiments with varying vent plugs. FIG. 2 shows a vent plug 900a, which is located at the end of the cylindrical inner wall 224a and fitted into a recess 301 in the housing interior non-patient wall 300. FIG. 3 shows a vent plug in a similar location to that of FIG. 2 however Vent plug 900b has a shoulder 901b. FIG. 4 shows a vent plug 900c that is located both within the cylindrical inner wall 224c and the recess 301 in the housing interior non-patient wall 300, and has a shoulder 901c. The vent plug location in each of these embodiments is such that no air can flow out of the flashback chamber 226 into the housing interior 220 without passing through the vent mechanism (900a,b,c).

Figure 5:
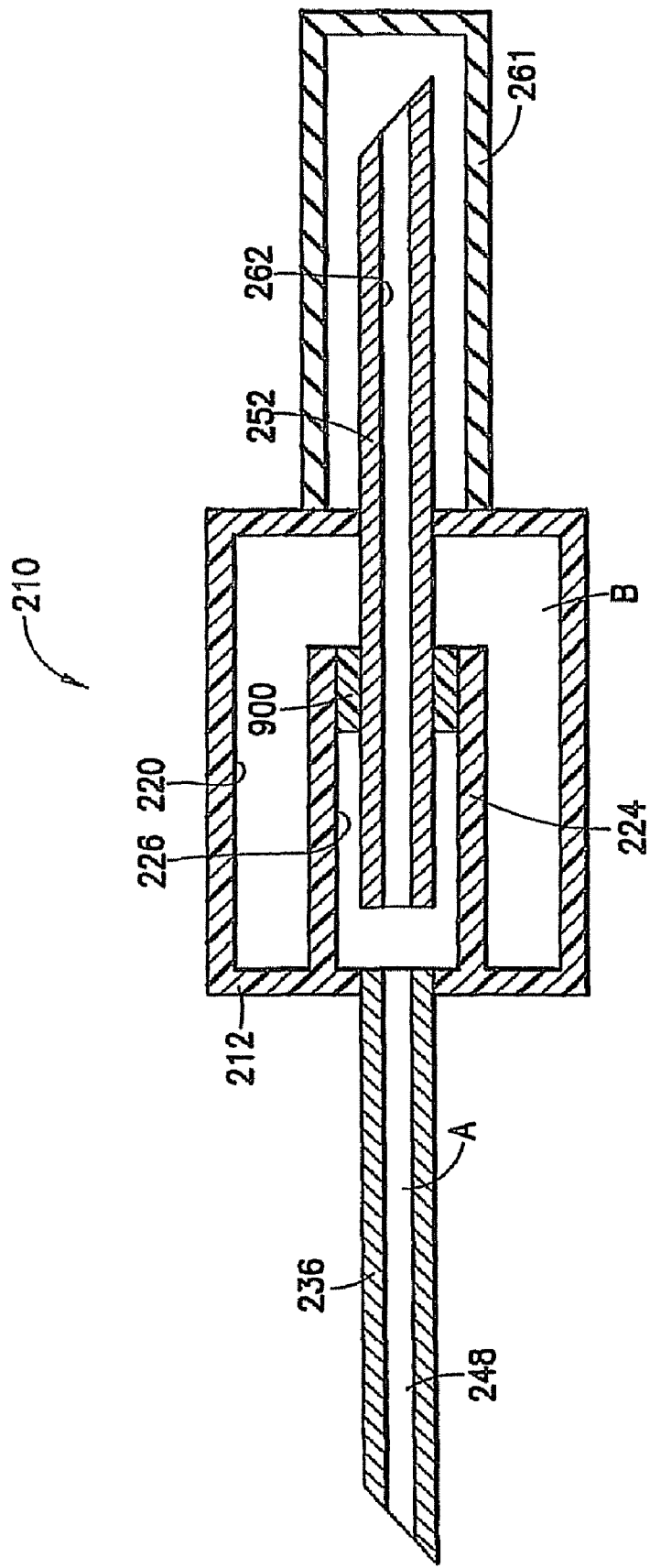
FIG. 5 is a schematic view of the needle assembly of FIG. 1 prior to use.
Figure 6:
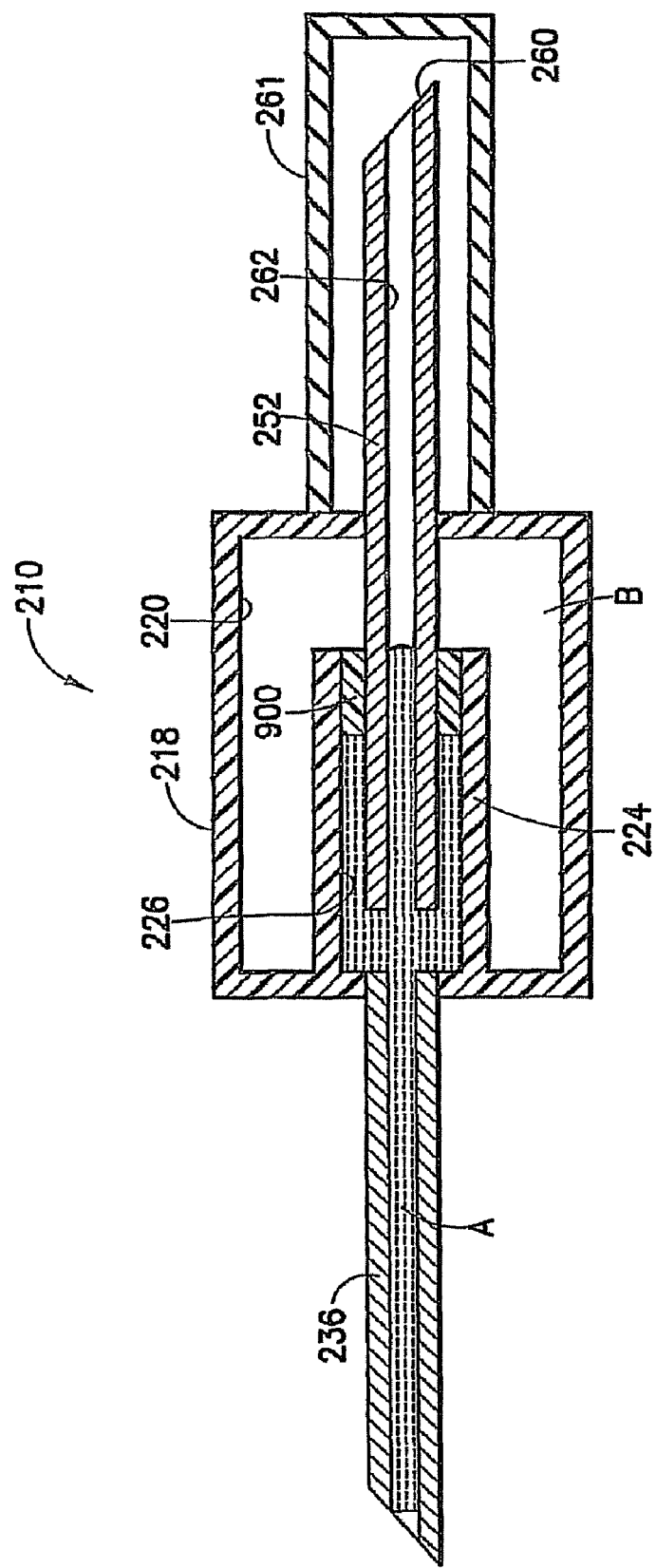
FIG. 6 is a schematic view similar to FIG. 5, but showing the first sign of venous entry.

FIGS. 5 and 6 provide schematic representations of the needle assembly 210 of FIG. 1 before and after a conventional venipuncture, in which, the needle assembly 210 is connected to a holder (not shown) and punctures the patient's skin to make a vein entry. Upon vein entry, blood enters the IV cannula 236 and flows toward the flashback chamber 226. The blood flows from inlet cannula 236 into the space between inlet and outlet cannula, such that blood flows both into the outlet cannula 252 and into flashback chamber 226. At this point in time, Flashback chamber 226 indicates successful vein entry and reduces the volume of air present in housing 212 shown in FIG. 6. Air that was at atmospheric pressure within the lumen of the N cannula 248, flashback chamber 226 housing interior 220 and the lumen of the non-patient cannula 262 prior to vein entry. Thus experiences compression due to the influence of venous pressure and this air is therefore forced through the IV cannula 236 shown in FIG. 6 into the flashback chamber 226 and through the vent plug into chamber 220. Blood flow into housing interior 220 is prevented by the vent plug 900, which allows the pressurized air to flow through it, but seals on contact with blood, thereby trapping the compressed air (at venous pressure) in housing interior 220. Blood flow in the entire needle assembly ceases once the pressure within chamber 226 and the venous pressure are equal.

Once the steps set forth in the previous paragraph occur, and venous entry is visually confirmed by the phlebotomist, an evacuated container (not shown), is then inserted into the holder such that exterior end 260 of second cannula 252 penetrates stopper of the container, as known in the art. Upon penetration of the stopper by second cannula 252, a negative pressure gradient is transmitted to chamber 226, causing blood to flow from chamber 226 into the container.

The needle assemblies described above desirably should be small for convenient use, but should be constructed to ensure reliable and rapid flashback. The occurrence of flashback in the needle assemblies described and illustrated above operate pursuant to the ideal gas law. In particular, at very low densities all gases and vapors approach ideal gas behavior and closely follow the Boyle's and Charles' laws given by:

$$P_1V_1 = P_2V_2$$

where:
- $P_1$ denotes the pressure of air within the needle assembly before needle insertion,
- $P_2$ denotes the pressure of air within the needle assembly after vein entry;
- $V_1$ denotes the volume of air within the needle assembly before vein entry; and
- $V_2$ denotes the volume of air within the needle assembly after vein entry.

Design parameters should keep the needle device as small as possible for easy use, while ensuring an appropriate volume as specified by the preceding equation. FIGS. 5 and 6 provide schematic representations of the needle assembly 210 of FIG. 1 for purposes of depicting the application of the ideal gas law. In this regard, A identifies the volume of lumen 248 through inlet cannula 236. B denotes the total volume of the housing interior 220, flashback chamber 226, lumen 242 through outlet cannula 252 and sealable sleeve 261. Referring again to the preceding equation, $P_1$ is the pressure within needle assembly 210 before use, and hence substantially equals atmospheric pressure. Atmospheric pressure will vary slightly from time to time and from location to location. However, for purposes of this analysis, atmospheric pressure $P_1$ will be assumed to be 760 mm Hg. $P_2$ in the preceding equation is the volume of the dead space in needle assembly 210 after vein entry. More particularly, after vein entry, blood will fill lumen 248 of inlet cannula 236, thereby reducing the volume to be occupied by gas in remaining portions of needle assembly 210 and hence increasing the pressure of air in the remaining portion of needle assembly 210. A needle assembly with dimensions approximately as shown in FIG. 1 will have a pressure $P_2$ of about 790 mm Hg at venous pressure (with tourniquet). $V_1$ in the preceding equation defines, the volume of the total dead spaced in needle assembly 210 before use, and hence will equal A+B as shown in FIG. 5. $V_2$ defines the dead space in the device after vein entry, and with lumen 248 of inlet cannula 236 filled with blood. Hence, $V_2$ in the preceding equation will equal B. These input parameters can be employed to define a minimum desired size for the respective components of needle assembly 200 as shown in the following application of the ideal gas law equation.

$$P_1V_1 = P_2V_2$$

$$P_1/P_2 = V_2/V_1$$

$$760/790 = B/(A+B)$$

$$0.962 = B/(A+B)$$

$$0.962(A+B) = B$$

$$0.038B = 0.962A$$

$$B = 25.3A$$

Therefore, dead space in housing 212, outlet cannula 252 and sleeve 261 advantageously is at least 25.3 times the volume defined by lumen 248 through inlet cannula 236, and most advantageously is about 26 times the volume of lumen 248. However, other configurations are possible and will function as described herein.

The immediate response when an evacuated tube is placed in communication with outlet cannula 252 is to draw blood from the vein into tube (not shown). The highest-pressure gradient is always maintained between the vein and the evacuated tube. An axially aligned inlet cannula 236 and outlet cannula 252, therefore provide an unobstructed path for blood flow from the vein into evacuated tube.

When the requisite tubes are filled with blood, the needle assembly is removed from the vein. The sealed nature of the vent plug 900 inhibits the pressurized air within housing interior 220 from then moving into the flashback chamber 226 and into the Inlet cannula 236, which could promote dripping of blood from the IV cannula tip.

Figure 7:
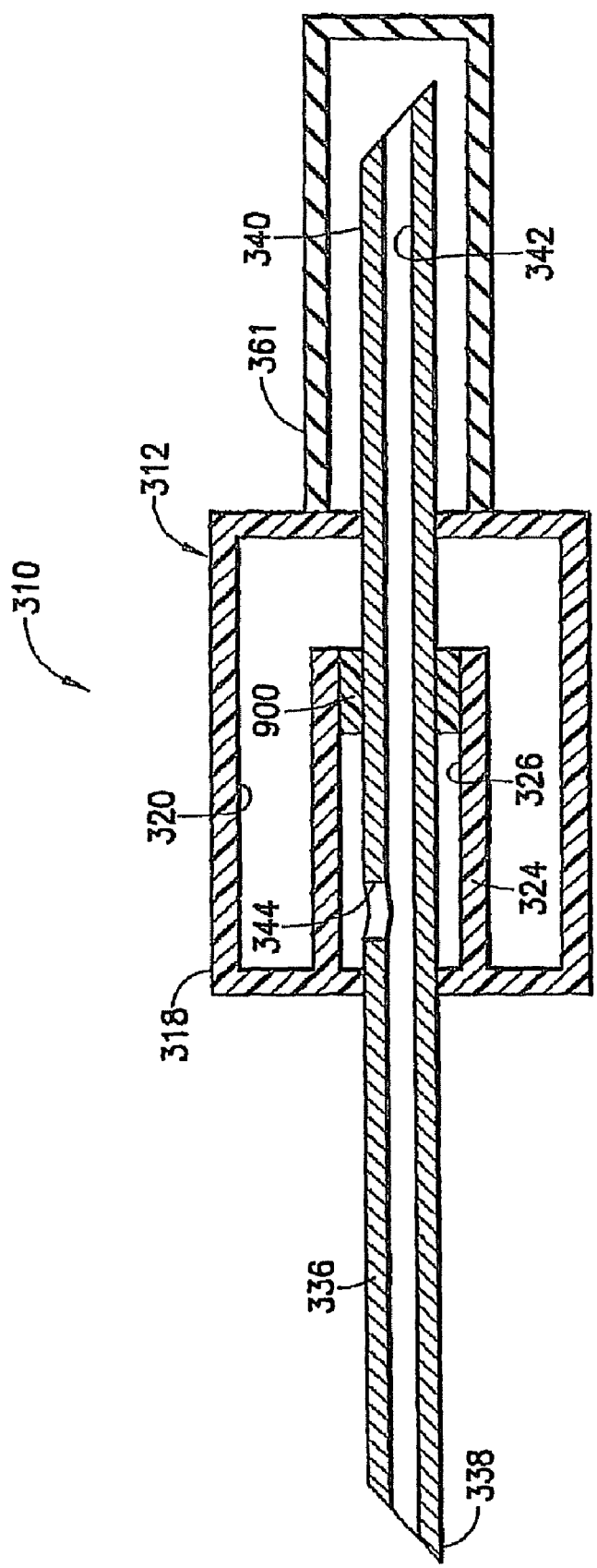
FIG. 7 is a schematic view of a fifth embodiment.

The preceding embodiments show structurally separate inlet and outlet cannulas that are axially aligned with one other and placed in close end-to-end relationship with one another. However, the principals of the invention described above also can be achieved with a single cannula formed with a transverse slot or aperture within the flashback chamber. For example, FIG. 7 schematically shows a needle assembly 310 with a housing 312 that is substantially identical to housing 212 described and illustrated above. Needle assembly 310 differs from needle assembly 210 in that a single double end needle cannula 336 is provided and passes entirely through housing 312. More particularly, needle cannula 336 includes a venous entry end 338, a non-patient end 340 and a lumen 342 extending therebetween. Portions of cannula 336 within inner wall 324 include a slot or aperture 344 to provide communication between lumen 342 and flashback chamber 336 within inner wall 324. Needle assembly 310 functions substantially in the same manner as needle assembly 210 described and illustrated above.

The relative dimensional calculations, volumes and pressures apply to both illustrated and unillustrated embodiments of the invention. Accordingly, the scope of the as defined by the appending claims is not limited to the specific illustrated embodiments. Various other changes and modifications may be effected therein by one skilled in the art without departing from the scope or spirit of the invention, and it is intended to claim all such changes and modifications as fall within the scope of the invention.

What is claimed is:
1. A needle assembly comprising:
a housing comprising a housing chamber defining an interior volume, a flashback chamber, and a vent mechanism separating the housing chamber from the flashback chamber;
a patient cannula end extending from a first end of the housing to the flashback chamber defining a patient cannula volume and a non-patient cannula end extending from a second end of the housing to the flashback chamber defining a non-patient cannula volume, said patient cannula end and non-patient cannula end both in fluid communication with the flashback chamber of the housing; and
a sleeve controlling fluid flow out of said non-patient cannula end,
wherein a first volume defined by the interior volume of the housing chamber, the flashback chamber, the non-pa- tient cannula end, and the sleeve is at least 25.3 times a second volume defined by the volume of the patient cannula end.

2. The needle assembly of claim 1, wherein the vent mechanism seals upon contact with blood.

3. The needle assembly of claim 1, wherein sleeve is mounted about the non-patient cannula end.

4. The needle assembly of claim 1, further comprising a first cannula comprising the patient cannula end and a second cannula comprising the non-patent cannula end, said first cannula having an interior end mounted in said housing chamber in fluid communication with said flashback chamber, said second cannula having an interior end into fluid communication with said flashback chamber.

5. The needle assembly of claim 4, wherein the interior ends of the first and second cannulae are separated by an axial gap.

6. The needle assembly of claim 5, wherein the axial gap has a length of at least 0.5 mm.

7. The needle assembly of claim 4, wherein the flashback chamber is defined at least in part by a cylindrical interior wall of the housing chamber surrounding the interior end of the second cannula forming a radial gap.

8. The needle assembly of claim 7, wherein the radial gap has a size of approximately 0.2 mm.

9. The needle assembly of claim 8, wherein the radial gap produces a laminar flow of blood within the flashback chamber to provide a magnified flashback indication with a small volume of blood.

10. The needle assembly of claim 1, wherein the flashback chamber is configured to produce a laminar flow of blood within the flashback chamber to provide a magnified flashback indication with a small volume of blood.

11. The needle assembly of claim 1, wherein the assembly comprises a single cannula comprising said patient cannula end and said non-patient cannula end, said single cannula mounted in said housing with an aperture in a side wall of said single cannula, said aperture in communication with said chamber.

12. The needle assembly of claim 1 wherein the housing chamber includes a wall portion that defines a predetermined interior volume.

13. A needle assembly comprising:
a housing comprising a housing chamber defining an interior volume, a flashback chamber, and a vent mechanism separating the housing chamber from the flashback chamber;
a first cannula mounted in said housing chamber, said first cannula having a patient end which extends exterior of the housing chamber and an interior end which extends into said flashback chamber; and
a second cannula mounted in said housing chamber, said second cannula having a non-patient end which extends exterior of the housing chamber and an interior end which extends into said flashback chamber, said second cannula mounted in axial alignment with said first cannula;
wherein said interior end of said first cannula and said interior end of said second cannula are separated by an axial gap having a length of at least 0.5 mm.

14. The needle assembly of claim 13, wherein the flashback chamber is configured to produce a laminar flow within the flashback chamber to provide a magnified flashback indication with a small volume of blood.

15. The needle assembly of claim 13 wherein the housing chamber includes a wall portion that defines a predetermined interior volume.

16. A method of flashback visualization for a blood collection needle assembly comprising:
providing a needle assembly for blood collection, said needle assembly comprising a housing comprising a housing chamber having a wall portion defining a predetermined interior volume, a flashback chamber, a vent mechanism separating the housing chamber from the flashback chamber, a patient cannula end extending from a first end of the housing to the flashback chamber defining a patient cannula volume and a non-patient cannula end extending from a second end of the housing to the flashback chamber defining a non-patient cannula volume, said patient cannula end and non-patient cannula end in fluid communication with the flashback chamber of the housing, and a sleeve mounted about the non-patient cannula end controlling fluid flow out of said non-patient cannula end;
providing a blood flow into the intravenous end of said cannula and into the chamber through said aperture such that air is pushed out of the cannula into the chamber, through the vent mechanism and into the housing interior; and
continuing the blood flow such that the blood contacts the vent mechanism and seals the vent mechanism against flow of air from said housing interior back into said chamber.

17. The method of claim 16 wherein a first volume defined by the interior volume of the housing chamber, the flashback chamber, the non-patient cannula end, and the sleeve is at least 25.3 times a second volume defined by the volume of the patient cannula end.

18. The method of claim 16 wherein said patient cannula end and non-patient cannula end each include an interior end and wherein said interior end of said patient cannula end and said interior end of said non-patient cannula end are separated by an axial gap having a length of at least 0.5 mm.

* * * * *